United States Patent [19]
Green

[11] Patent Number: 6,089,947
[45] Date of Patent: Jul. 18, 2000

[54] CLOTH FIGURE WITH SCENTED PELLETS

[76] Inventor: Dennis E. Green, 102 Falcon Hills Dr., Highlands Ranch, Colo. 80126

[21] Appl. No.: 09/358,050

[22] Filed: Jul. 21, 1999

[51] Int. Cl.[7] .............................. A63H 3/00; A01K 29/00; A24F 25/00
[52] U.S. Cl. .............................. 446/268; 119/711; 239/60
[58] Field of Search .................... 446/268, 296, 446/369; 119/707, 711; 928/905; 239/60, 34

[56] References Cited

U.S. PATENT DOCUMENTS

| | | |
|---|---|---|
| 1,441,095 | 1/1923 | Kahnweiler .............................. 119/711 |
| 1,534,964 | 4/1925 | Kahnweiler .............................. 119/711 |
| 1,743,827 | 1/1930 | Mercogliano . |
| 2,200,840 | 5/1940 | Frank . |
| 2,618,892 | 11/1952 | Locks et al. . |
| 3,945,568 | 3/1976 | Bychowski . |
| 4,419,395 | 12/1983 | Sugimoto . |
| 4,465,232 | 8/1984 | Field . |
| 4,612,223 | 9/1986 | Spector . |
| 5,037,343 | 8/1991 | Benites . |
| 5,676,583 | 10/1997 | Wang et al. . |
| 5,758,604 | 6/1998 | Jorgensen ............................... 119/711 |

*Primary Examiner*—D. Neal Muir
*Attorney, Agent, or Firm*—Dorr, Carson, Sloan & Birney, P.C.

[57] ABSTRACT

An air freshener for use in an automobile, home, or office representing an animal, cartoon character, or other figure. At least one scent-releasing capsule is inserted through a mouth formed within a body of the figure and retained therein. Optionally the body can have a distinct head member. Likewise, a hanger can be provided from which to hang the air freshener. The scent-releasing capsule releases scent through the air-permeable body and into the surrounding air. Additional fresh capsules can be inserted through the mouth and retained by the body member when the scent-releasing capsule has been spent.

6 Claims, 2 Drawing Sheets

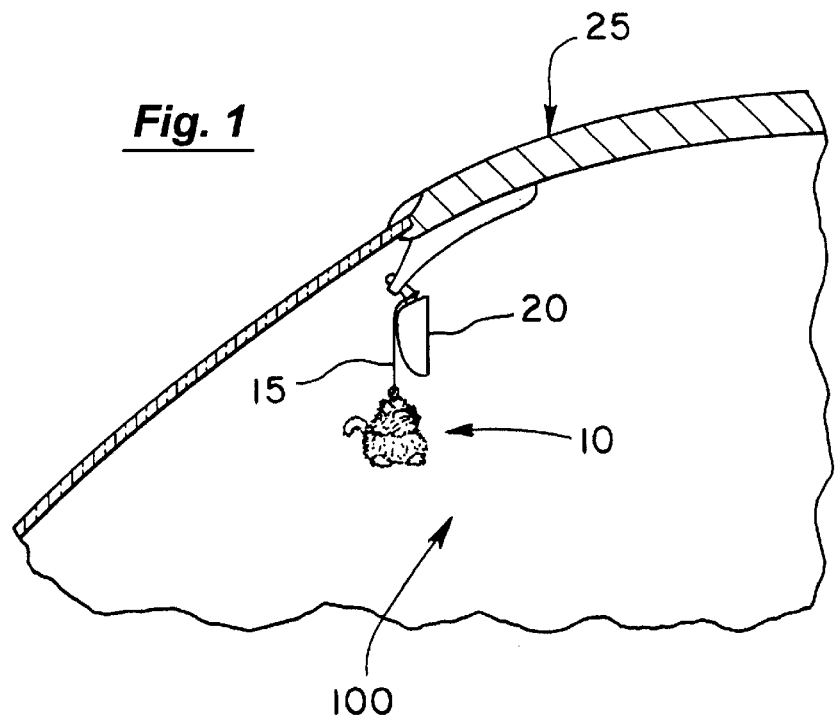
*Fig. 1*
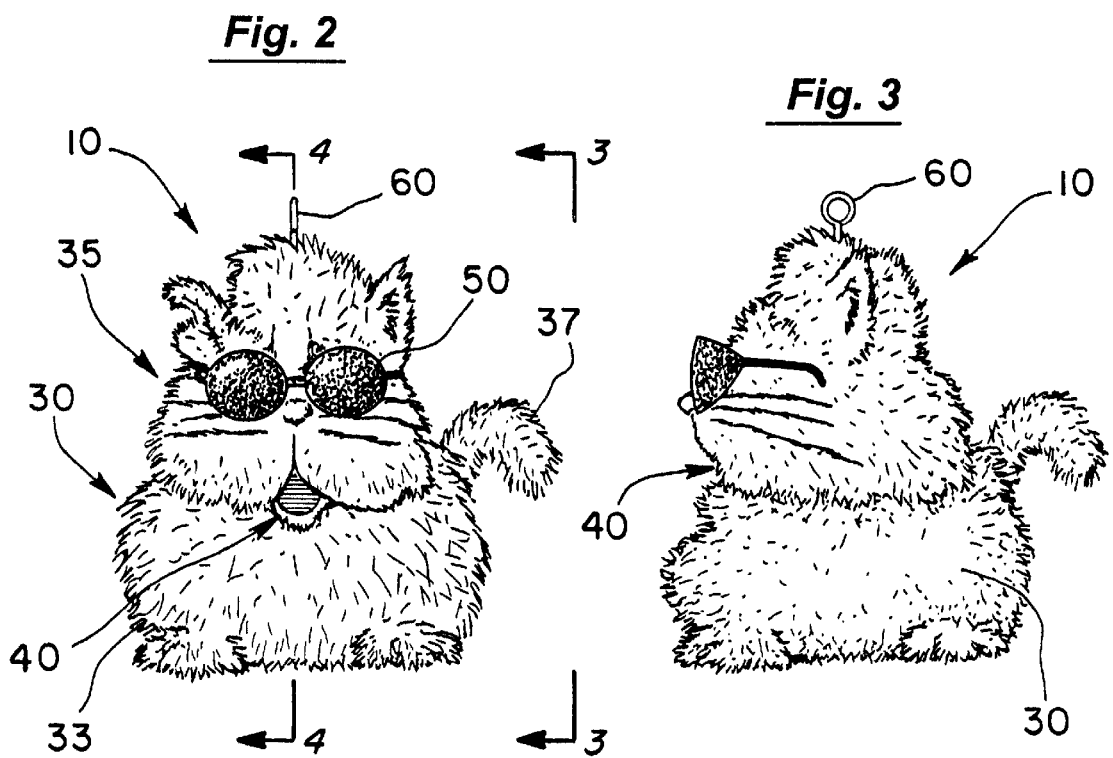
*Fig. 2*
*Fig. 3*

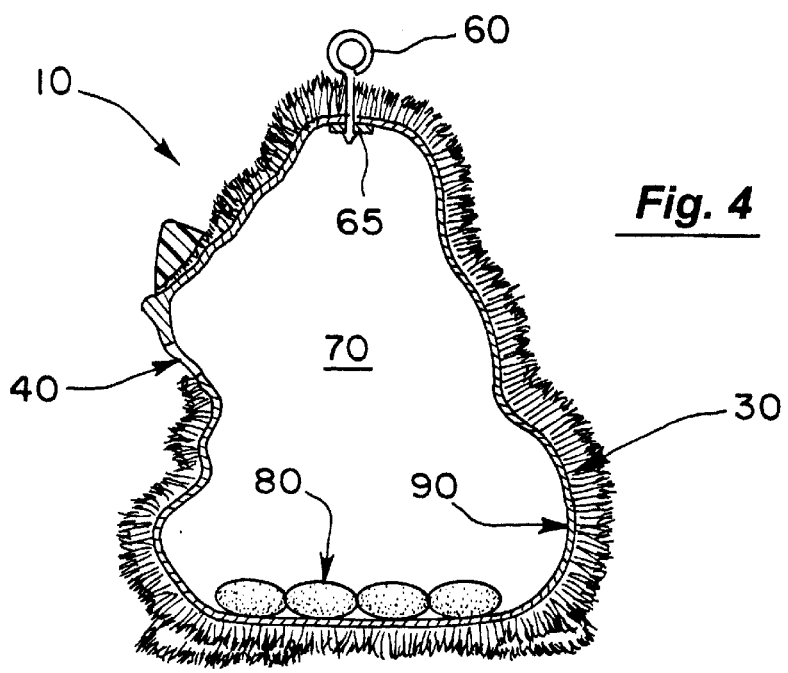
*Fig. 4*
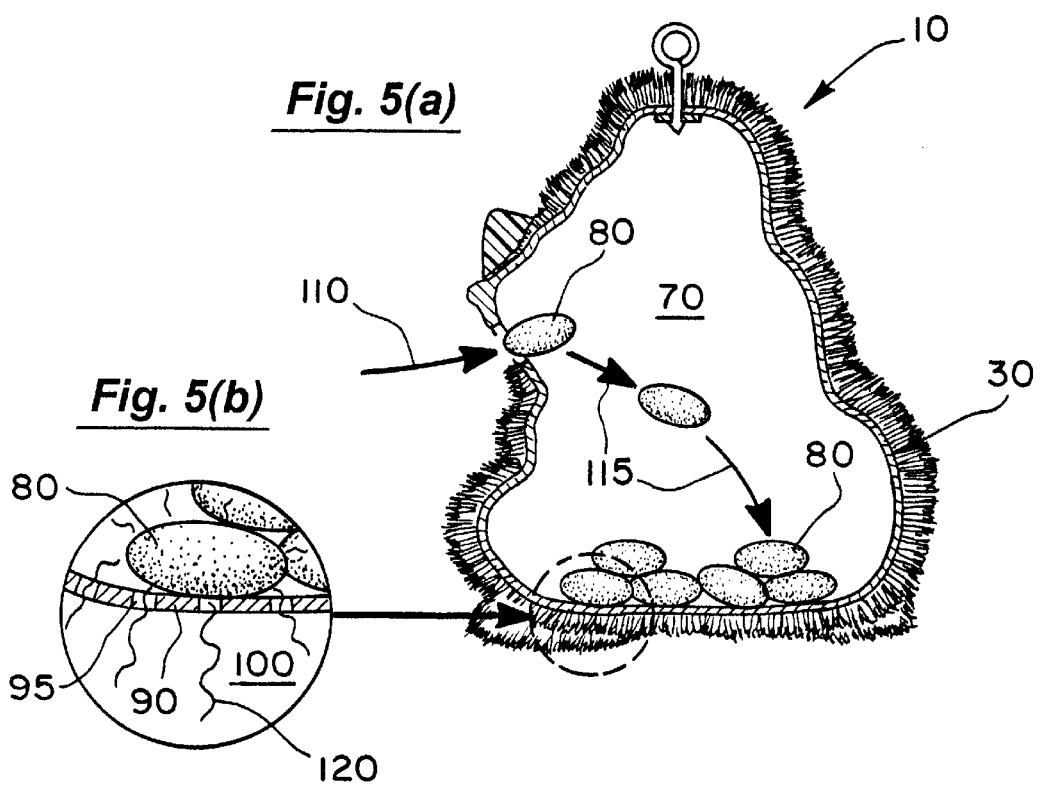
*Fig. 5(a)*
*Fig. 5(b)*

CLOTH FIGURE WITH SCENTED PELLETS

BACKGROUND OF THE INVENTION

1. Field of the Invention

The present invention relates generally to the field of air fresheners. More specifically, the present invention discloses a reusable air freshener representing an animal, cartoon character, or fanciful figure, and having a hollow interior cavity for receiving scented pellets.

2. Statement of the Problem

Air fresheners are commonly used throughout the world, especially in locations that receive little ventilation (e.g., automobiles). However, air fresheners do not release scent perpetually and must therefore either be disposed of or refilled once spent. Some air fresheners include a refillable member that retains a scented element. Hence, when the scented element is spent, or no longer releases sufficient scent, the spent element can be disposed of and replaced with a fresh scented element. However, such refillable air fresheners generally require the spent element be removed from the refillable member before a fresh element can be added. In addition, such refillable members are often too bulky or heavy to be used effectively in an automobile. In addition, most air fresheners are mostly functional in appearance and therefore offer no entertainment value.

Air fresheners have been used in the past, including the following:

| Inventor | Patent No. | Issue Date |
| --- | --- | --- |
| Mercogliano | 1,743,827 | Jan. 14, 1930 |
| Frank | 2,200,840 | May 14, 1940 |
| Locks et al. | 2,618,892 | Nov. 25, 1952 |
| Bychowski | 3,945,568 | Mar. 23, 1976 |
| Sugimoto | 4,419,395 | Dec. 6, 1983 |
| Field | 4,465,232 | Aug. 14, 1984 |
| Spector | 4,612,223 | Sep. 16, 1986 |
| Benites | 5,037,343 | Aug. 6, 1991 |
| Wang et al. | 5,676,583 | Oct. 14, 1997 |

Mercogliano discloses an insecticide or disinfectant container for use on upholstered furniture.

Frank discloses a scented cord-like sachet device having an outer fabric casing. The interior of the casing is either filled with a long-fibred scent carrier or sachet powder.

Locks et al. disclose a resilient doll containing a hollow rubber bulb 22 that holds pieces of a liquid-absorbent spongy material 25 that have been saturated with an aromatic substance. Squeezing the doll compresses the rubber bulb 22 inside and expels odor-bearing air from the aperture 24 (i.e., mouth) of the doll. The pieces of spongy material are described as being larger than the dimensions of the aperture 24, so that they cannot be removed from the doll.

Bychowski discloses a scented Christmas tree ornament for holding liquid pine scent.

Sugimoto discloses a perfumed pendant having front and back vinyl layers with an intermediate layer of resilient foam padding to give a three-dimensional appearance to the pendant. A "capsulated perfume layer" is laminated to the front vinyl layer.

Field discloses an adornment having a rear face with an adhesive layer that can be affixed to another surface. The front face of the adornment has a pocket for holding a scented element, such as a scent-saturated capsule or a scent-filled capsule.

Spector discloses a reversible fragrance emitting unit containing fragrance emitting pellets.

Benites discloses a scented figure (e.g., a skunk) with a tail having a cavity. The cavity includes a series of slits for releasing an aromatic scent from micro-capsules on a scent strip. The scent strip can be removed from the cavity in the tail by opening a zipper.

Wang et al. disclose a doll with a removable scent cartridge.

3. Solution to the Problem

None of the prior art references uncovered in the search show an air freshener that represents an animal, cartoon character, or other figure having an air-permeable body with an internal cavity and a mouth leading to the internal cavity to receive a scented pellet that releases a permeating scent to the ambient air.

SUMMARY OF THE INVENTION

This invention provides an air freshener representing a figure, such as an animal, cartoon character, or other figure having a body and a mouth. The body of the air freshener is made of an air-permeable material and forms an internal cavity within the body. A mouth leads through the body and into the internal cavity so that a scented pellet can be inserted through the mouth and retained within the internal body cavity. The scented pellet then releases a permeating scent to the ambient or surrounding air. Once spent, fresh pellets can be added through the mouth. In a preferred embodiment, the mouth is a "one-way" mouth so that pellets do not fall out of the internal cavity from the mouth once inserted. In particular, the size of the mouth can be selected so that it requires a degree of effort to remove pellets, as opposed to allowing the pellets to accidentally fall out of the internal cavity.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 1 is a perspective view of an air freshener of the present invention shown hanging from the rear-view mirror of an automobile.

FIG. 2 is a front view of the air freshener.

FIG. 3 is a side view of the air freshener taken along lines 3—3 of FIG. 2.

FIG. 4 is a cross-sectional view of the air freshener taken along lines 4—4 of FIG. 2.

FIG. 5a is a cross-section view of the air freshener showing a scented pellet inserted through the mouth and into the internal cavity.

FIG. 5b is a detailed view of the air-permeable material of the air freshener shown in FIG. 5a in which the scent from the scented pellet is permeating the body.

DETAILED DESCRIPTION OF THE INVENTION

The air freshener 10 of the present invention is shown in FIG. 1 hanging 15 from a rear-view mirror 20 of automobile 25. It is to be expressly understood that the air freshener 10 can be hung or otherwise situated in any suitable manner within the automobile 25. Likewise, the air freshener 10 can be used in homes, offices, or other areas where it is desirous to provide scent to the surrounding ambient air.

The air freshener 10 is shown in the form of a cartoon representation of a cat. Other representations can also be used (e.g., a dinosaur, dog, duck, bear, cartoon characters, etc.) under the teachings of the present invention. Likewise, although in the preferred embodiment the air freshener 10 is a representation of an animal, other suitable representations of a cartoon character, person, or other object having a body and mouth are contemplated within the scope of the present invention, and should be included within the meaning of the word "figure" as used herein.

The air freshener 10 of the present invention is shown in more detail in FIGS. 2 and 3. The air freshener 10 is comprised of a body 30 having a mouth 40 (e.g., a passageway or opening into the body 30) formed therein. The body can be further comprised of a distinct abdominal member 33 and head member 35. Any other extremities (e.g., tail 37) or decorations (e.g., sunglasses 50, clothes, etc.) can also be affixed to the body 30 of the air freshener 10. In addition, a hanger 60 (e.g., attached with clip 65 as shown in FIG. 4) or other suitable attachment device for attaching the air freshener 10 to the automobile 25 or other suitable location is also shown connected to the body 30. Alternatively, the air freshener 10 can be suspended from the windshield or window of a vehicle by means of a suction cup. The air freshener 10 can also simply be set in a desired location, such as the dashboard of a vehicle, or on furniture or a vanity in the home or office. This allows the hanger 60 may be omitted, if desired.

As shown in FIG. 4, a hollow interior cavity 70 is formed within the body 30. A scented pellet or capsule 80 is inserted through the mouth 40 and retained within the hollow interior cavity 70 by an air-permeable material 90 which forms the body 30. The air-permeable material 90 can be any suitable fabric (e.g., "plush" used for stuffed-toy animals) or other material including a mesh or netting (wire, plastic, fabric, or otherwise), perforated plastic, etc. that retains the pellet 80 within the body 30 while providing sufficient air-permeability so that scent from the pellet 80 is dispersed to the surrounding air 100, as discussed below with reference to FIG. 5b.

It is to be expressly understood that the internal cavity 70 can be any size or shape and can include both the interior cavity formed by the abdominal member 33 and the head member 35 (as shown in FIGS. 4 and 5, or any combination thereof. Furthermore, any suitable scented pellet 80 can be used under the teachings of the present invention. For instance, the scented pellet 80 can be a scented paper ball, a gel capsule, etc. Likewise, the scented pellet 80 can be impermeable to air until broken, thus releasing scent only once broken (e.g., similar to conventional smelling-salt capsules commonly used in hospitals), or simply dissolve as scent is dispersed to the surrounding air 100. Similarly, the number of scented pellets 80 is immaterial to the present invention and only limited by personal preference (e.g., if a stronger scent is desired, more scented pellets 80 can be used and vice-versa) and the dimensions of the scented pellets 80 and the cavity 70.

FIG. 5a shows the air freshener 10 being "fed" with the scented pellet 80. The air freshener can be shipped to the consumer with the scented pellet 80 already retained within the cavity 70 of body 30 or shipped empty. In any event, the user can add the scented pellet 80 to the cavity 70 by inserting 110 the scented pellet 80 through the mouth 40. Once inserted through the mouth 40, the scented pellet 80 falls 115 into the cavity 70 and is retained therein by the air-permeable material 90. As shown in FIG. 5b, the scented pellet 80 gradually releases scent 120, which permeates 95 the air-permeable material 90 into the surrounding or ambient air 100. After the scent 120 from the scented pellet 80 has dissipated to the extent that scent 120 is no longer effectively released from the air freshener 10, a fresh scented pellet 80 can be added. This process can be repeated until the interior cavity 70 is full.

In the preferred embodiment, the mouth 40 is a "one-way" orifice into the body 30. That is, the mouth 40 allows the pellets to be inserted therethrough and into the internal cavity 70 while keeping the pellets 80 from falling back through the mouth 40 once in the internal cavity 70. Any convention method for doing so can be used. For example, a slotted cloth may be affixed over the mouth 40 from within thus allowing the pellet 80 to be pushed through the slot, but covering the mouth sufficiently so that the pellets 80 within the internal cavity 70 do not readily fall out from the mouth 40. Other suitable coverings will occur to those skilled in the art, such as a flexible slotted rubber covering, a sliding cover (spring-loaded or otherwise), a sliding drawer, a plug, etc. Alternatively, the mouth 40 can simply be dimensioned so that the pellet 80 only readily fits through the mouth 40 in one orientation (e.g., lengthwise).

The above disclosure sets forth a number of embodiments of the present invention. Other arrangements or embodiments, not precisely set forth, could be practiced under the teachings of the present invention and as set forth in the following claims.

I claim:

1. An air freshener representing a figure having a body and a mouth, said air freshener comprising:

an air-permeable body of said figure;

at least one scent-releasing pellet;

a cavity formed within said air-permeable body;

a one-way orifice formed in the shape of a mouth and leading through said body and into said cavity, said scent-releasing pellet retained within said cavity after said scent-releasing pellet has been inserted through said mouth, scent from said scent-releasing pellet released through said air-permeable body member into the surrounding air.

2. The air freshener of claim 1 wherein said body member comprises a distinct head portion of said figure.

3. The air freshener of claim 1 wherein said air-permeable body is made of a plush fabric.

4. The air freshener of claim 1 wherein said air-permeable body is made of a mesh material.

5. The air freshener of claim 1 further comprising a hanger attached to said body for hanging said air freshener.

6. The air freshener of claim 1 wherein said scent-releasing pellet is a paper ball.

* * * * *